(12) United States Patent
Gakh et al.

(10) Patent No.: US 8,362,047 B1
(45) Date of Patent: Jan. 29, 2013

(54) ANTI-CANCER AGENTS BASED ON 4-(HETERO)ARYl-1,2,5-OXADIAZOL-3-YL AMINO DERIVATIVES AND A METHOD OF MAKING

(75) Inventors: Andrei A. Gakh, Bethesda, MD (US); Mikhail Krasavin, Moscow Region (RU); Ruben Karapetian, Moscow (RU); Konstantin A. Rufanov, Moscow (RU); Igor Konstantinov, Moscow (RU); Elena Godovykh, Rostov-na-Donu (RU); Olga Soldatkina, Moscow (RU); Andrey V. Sosnov, Moscow (RU)

(73) Assignee: U.S. Department of Energy, Washington, DC (US)

( * ) Notice: Subject to any disclaimer, the term of this patent is extended or adjusted under 35 U.S.C. 154(b) by 23 days.

(21) Appl. No.: 12/822,243

(22) Filed: Jun. 24, 2010

(51) Int. Cl.
*A61K 31/4184* (2006.01)
*A61K 31/42* (2006.01)
*C07D 271/04* (2006.01)
*C07D 235/08* (2006.01)
(52) U.S. Cl. ...... 514/364; 514/394; 548/125; 548/304.7
(58) Field of Classification Search .................. 514/364, 514/394; 548/125, 304.7
See application file for complete search history.

(56) References Cited

PUBLICATIONS

STN Chem Abstract database on Jun. 17, 2004, CAS RN 694485-42-2.*
Vippagunta et al., Advanced Drug Delivery Reviews, p. 3-27.*
Wu and Farrelly, Toxicology 236:1-6, 2007.*
A compound with CAS RN 385383-22-2_(2002).*
Yoon et al., Journal of BioMolecular Screening (2008), 13(7), p. 591-608.*

* cited by examiner

*Primary Examiner* — Yong Chu
(74) *Attorney, Agent, or Firm* — Mark C. Lang; Bradley W. Smith; John T. Lucas

(57) ABSTRACT

The present disclosure relates to novel compounds that can be used as anti-cancer agents in the prostate cancer therapy.

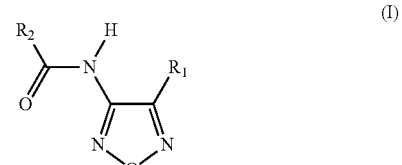

(I)

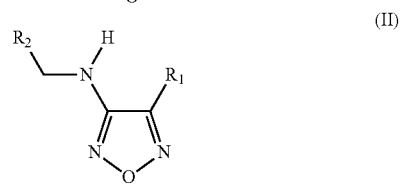

(II)

In particular, the invention relates N-substituted derivatives of 4-(hetero)aryl-1,2,5-oxadiazol-3-yl amines having the structural Formula (I) and (II), stereoisomers, tautomers, racemics, prodrugs, metabolites thereof, or pharmaceutically acceptable salt and/or solvate thereof. Meaning of R1 and R2 in the Formula (I) and (II) are defined in claim 1. The invention also relates to methods for preparing said compounds, and to pharmaceutical compositions comprising said compounds.

6 Claims, No Drawings

ANTI-CANCER AGENTS BASED ON 4-(HETERO)ARY1-1,2,5-OXADIAZOL-3-YL AMINO DERIVATIVES AND A METHOD OF MAKING

CONTRACTUAL ORIGIN OF THE INVENTION

The U.S. Government has certain rights in the present invention pursuant to Contract No. #3548 between the Department of Energy (DOE) (International Science and Technology Center) and the Chemical Diversity Research Institute, dated Jul. 1, 2007.

FIELD OF INVENTION

The present invention relates to novel anti-cancer agents based on N-substituted derivatives of 4-(hetero)aryl-1,2,5-oxadiazol-3-yl amines that can be used in prostate cancer therapy. The present invention also relates to methods of preparing said compounds, and to pharmaceutical compositions comprising said compounds.

BACKGROUND OF THE INVENTION

Cancer is the second leading cause of human death next to coronary disease. Worldwide, millions of people die from cancer every year. In the United States alone, as reported by the American Cancer Society, cancer causes the death of well over half-million people annually, with over 1.2 million new cases diagnosed per year. While deaths from heart disease have been declining significantly, those resulting from cancer generally are on the rise. In this century, cancer is predicted to become the leading cause of death.

Prostate cancer is the number one cancer diagnosed in men today. While it occurs to certain extent throughout the world (least commonly in Eastern/Southern Asia), it is viewed as the major public health threat in Western Europe and, especially, the United States. In the US alone, it has been projected that 186,320 new cases of prostate cancer (mostly—among men over fifty) will have been diagnosed in 2008, accounting for 25% of all cancers diagnosed in men that year and 10% of the total cancer-related mortality. Appropriate diet (including dietary supplements) and exercise are currently the common themes for prostate cancer prevention while classical treatments are limited to surgery, radiation therapy, and hormone therapy.

Chemotherapy of late-stage prostate cancer is still largely experimental; however, it may lead to increased survival in the future. Specifically, small molecules as well as antibodies targeted at disrupting vital signaling pathways in cancerous cells have a potential to provide new basis for innovative treatment of prostate cancer and other proliferative disorders in the years to come. As a result, there is a strong need for new compound classes that can be used for hormone-refractory prostate cancer chemotherapy. We have discovered that 4-(hetero)aryl-1,2,5-oxadiazol-3-yl amino derivatives are effective in vitro against androgen-independent prostate cancer cell lines.

SUMMARY OF THE INVENTION

The present invention relates to novel compounds (N-substituted derivatives of 4-(hetero)aryl-1,2,5-oxadiazol-3-yl amines) having the structural Formula (I) and (II), stereoisomers, tautomers, racemics, prodrugs, metabolites thereof, or pharmaceutically acceptable salt and/or solvate thereof,

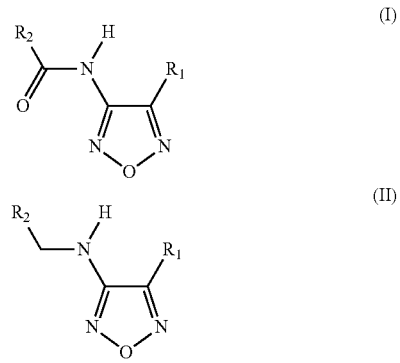

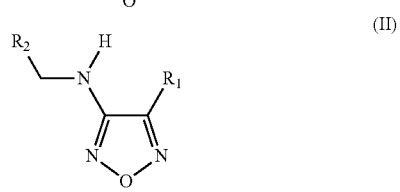

Wherein:

$R_1$ is selected from substituted or non-substituted aryls, in particular to phenyl groups bearing electron-donating substituents, and heteroaryls, in particular to substituted or non-substituted imidazols fused to substituted or non-substituted aromatic ring to form bicyclic heterocycles of the general formula (III), (IV), (V), (VI), (VII) and (VIII):

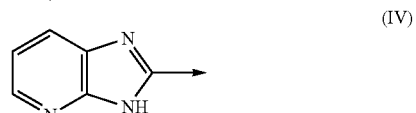

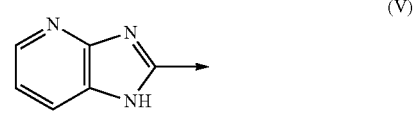

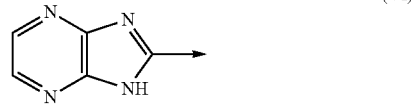

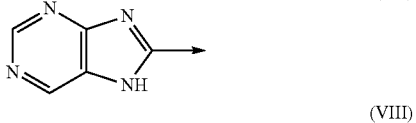

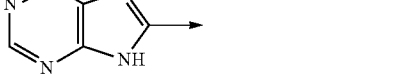

$R_2$ is selected from substituted or non-substituted, fused or non-fused to substituted or non-substituted aromatic ring, aryl or heteroaryl groups. Acceptable salts are hydrochloride, citrate, maleate or similar salts listed, for example in the Handbook of Pharmaceutical Salts Properties, selection and use—Stahl P H, Wermuth C G, editors. 2002. Weinheim/Zurich: Wiley-VCH/VHCA. Typical solvate is hydrate (water).

The compounds have been prepared and, upon screening for their biological activity, exhibited inhibition of DU-145 cell proliferation in dose-response.

The invention also relates to methods for preparing said compounds, and to pharmaceutical compositions comprising said compounds.

DETAILED DESCRIPTION OF THE INVENTION

The present invention is a result of our ongoing efforts to find novel antiproliferative agents as potential treatments for cancer. It was aimed at identifying new small heterocyclic molecules in ChemDiv, Inc. collection that would be specifically inhibitory to DU-145 human prostate carcinoma cell line (a 'classical' cell line of prostate cancer) while exhibiting no non-specific (general) cytotoxicity. High-throughput screening of a highly diverse set of over 7,000 compounds comprising over 200 chemical classes led to several confirmed hit classes.

Among these, two closely related 1,2,5-oxadiazol compounds, (I) and (II),

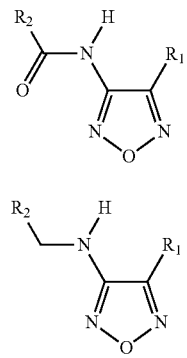

Wherein:

R1 is selected from substituted or non-substituted aryls, in particular to phenyl groups bearing electron-donating substituents, and heteroaryls, in particular to substituted or non-substituted imidazols fused to substituted or non-substituted aromatic rings to form bicyclic heterocycles of the general formula (III), (IV), (V), (VI), (VII) and (VIII):

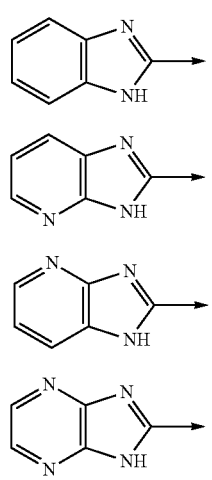

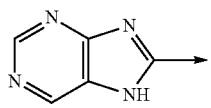

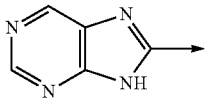

R2 is selected from substituted or non-substituted, fused or non-fused to substituted or non-substituted aromatic ring, aryl or heteroaryl groups.

The compounds exhibited inhibition of DU-145 cell proliferation in dose-response manner, attracted our attention due to their drug-likeness, structural simplicity, presence in their structure of two distinct types of peripheral appendages (thus allowing for informative SAR exploration), and syntheses reported in the literature for related structures.

The preferred sequence for chemical synthesis of these N-substituted derivatives of 4-(hetero)aryl-1,2,5-oxadiazol-3-yl amines compounds is shown below. The commercially available chloroanhydrides R1COCl (R1-acyl chlorides) are converted in three steps to 4-(hetero)aryl-1,2,5-oxadiazol-3-amines, that by acylation with commercially available chloroanhydrides R2COCl (R2-acyl chlorides) under mild conditions produce (I) in overall low to moderate yields. Further reduction of carbonyl group leads to amines (II).

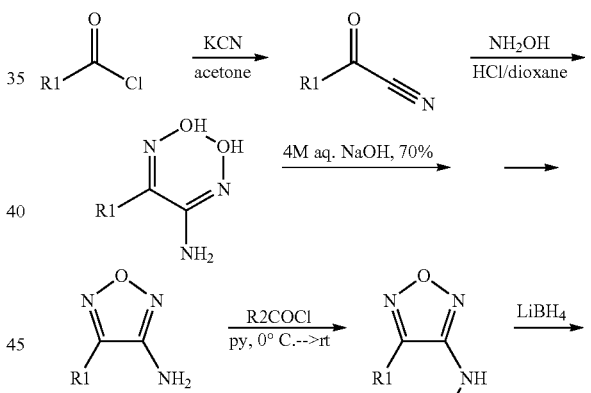

The general protocol: to a stirred suspension of KCN (potassium cyanide) (13 g, 0.2 mol) in dry acetone (200 mL) a solution of R1COCl (R1-acyl chloride) (0.1 mol) in dry acetone (100 mL) was added drop-wise over a period of 3-4 hours, at ambient temperature. After completion, the stifling of the reaction mixture was continued overnight followed by filtration of inorganic solids and evaporation of acetone under reduced pressure, to produce R1-substituted carbonyl cyanides. Typical yields vary in a range of 85-100 wt. %. The obtained carbonyl cyanide (50 mmol) is dissolved in 1,4-dioxane (50-150 mL) and 50 wt. % aq. hydroxylamine ($NH_2OH$) (200 mmol) was added, followed by addition of catalytic (4 mmol) amount of 4M HCl (hydrochloric acid) in 1,4 dioxane (1 mL). The reaction mixture was heated at 50° C. for 12 hr and allowed to cool down to ambient temperature overnight. The obtained precipitate of bis-oxime was collected by filtration, washed with dioxane and dried with air. Typical yields on this step vary in the range of 50-60 wt. %. The crude bis-oxime (30 mmol) was added in portions to vigorously stirred 4M aq. NaOH (sodium hydroxide) (100 mL) under inert atmosphere (nitrogen gas). The reaction completes in 5-20 hr. The reaction mixture is neutralized by addition of aq. $NaHSO_4$ (sodium hydrogen sulfate) (400 mmol) and thus obtained oxadiazol is extracted with EtOAc (ethyl acetate). The product is purified by FC (flash chromatography) on silica gel using mixtures of hexane/EtOAc as mobile phases. Yields of purified oxadiazols vary up to 70 wt. %. Further acylation with R2COCl was carried out on 20 mmol scales by a typical procedure using dry pyridine as both solvent and base. Purification was achieved by CC (chromatography) on silica gel between 0° C. and room temperature. Overall yields of (I) vary in the range of 9-27 wt. % (see examples 1-12 listed below). Further reduction of (I) to form (II) has been achieved in typically high yields by stirring with a double molar excess of $LiBH_4$ (2.0 M solution in tetrahydrofurane: Aldrich, Cat. Nr. 230200), followed by quenching with water, extraction of (II) with EtOAc (ethyl acetate) and purification by FC (flash chromatography) on silica gel using mixtures of hexane/EtOAc as mobile phases. Both (I) and (II) correspond off-white to yellow colored solids of >95% purity, confirmed by $^1$H-NMR analysis of the solutions of 5 mg of I in DMSO-d6 (0.25 mL) using Bruker DPX-400 instrument (400 MHz H1 NMR Frequency).

While there are potentially many different N-substituted derivatives of 4-(hetero)aryl-1,2,5-oxadiazol-3-yl amines that can be prepared under the scope of the present invention, depending on the combinations of R1-acyl chlorides and R2-acyl chlorides, suitable N-substituted derivatives of 4-(hetero)aryl-1,2,5-oxadiazol-3-yl amines are (but not meant to be limited to): 2-Chloro-$N^1$-[4-(1-butyl-1H-1,3-benzimidazol-2-yl)-1,2,5-oxadiazol-3-yl]benzamide; 2-Chloro-$N^1$-[4-(1-isobutyl-1H-1,3-benzimidazol-2-yl)-1,2,5-oxadiazol-3-yl]benzamide; 2-Chloro-$N^1$-[4-(1-allyl-1H-1,3-benzimidazol-2-yl)-1,2,5-oxadiazol-3-yl]benzamide; Ethyl 2-(2-4-[(2-fluorobenzoyl)amino]-1,2,5-oxadiazol-3-yl-1H-1,3-benzimidazol-1-yl)acetate; 2-Ethoxy-$N^1$-[4-(4-methoxyphenyl)-1,2,5-oxadiazol-3-yl]benzamide; 2-Propoxy-$N^1$-[4-(4-methoxyphenyl)-1,2,5-oxadiazol-3-yl]benzamide; 2-Ethoxy-$N^1$-[4-(4-ethoxyphenyl)-1,2,5-oxadiazol-3-yl]benzamide; 2-Propoxy-$N^1$-[4-(4-ethoxyphenyl)-1,2,5-oxadiazol-3-yl]benzamide; 2-Butoxy-$N^1$-[4-(4-ethoxyphenyl)-1,2,5-oxadiazol-3-yl]benzamide; 2-Ethoxy-$N^1$-[4-(4-ethoxy-3-methylphenyl)-1,2,5-oxadiazol-3-yl]benzamide; 2-Propoxy-$N^1$-[4-(4-ethoxy-3-methylphenyl)-1,2,5-oxadiazol-3-yl]benzamide; and 5-chloro-$N^2$-[4-(4-ethoxyphenyl)-1,2,5-oxadiazol-3-yl]-3-methyl-1-benzofuran-2-carboxamide.

Suitable R1-acyl chlorides (R1 chloroanhydrides) are (but are not limited to): 1-butyl-1H-1,3-benzimidazole-2-carbonyl chloride; 1-isobutyl-1H-1,3-benzimidazole-2-carbonyl chloride; 1-allyl-1H-1,3-benzimidazole-2-carbonyl chloride; ethyl 2-[2-(chlorocarbonyl)-1H-1,3-benzimidazol-1-yl]acetate; 4-methoxy-1-benzenecarbonyl chloride; 4-ethoxy-1-benzenecarbonyl chloride; or 4-ethoxy-3-methyl-1-benzenecarbonyl chloride.

Suitable R2-acyl chlorides (R2 chloroanhydrides) are (but are not limited to): 2-chloro-1-benzene-carbonyl chloride; 2-fluoro-1-benzenecarbonyl chloride; 2-ethoxy-1-benzenecarbonyl chloride; 2-propoxy-1-benzene-carbonyl chloride; 2-butoxy-1-benzene-carbonyl chloride; and 5-chloro-3-methyl-1-benzofuran-2-carbonyl chloride.

EXAMPLES

In the Examples set forth below, the reaction of R2-acyl chlorides with either R1-acyl chlorides, or the same or different R2-acyl chlorides, is accomplished using the general protocol set forth above.

Example 1

2-Chloro-$N^1$-[4-(1-butyl-1H-1,3-benzimidazol-2-yl)-1,2,5-oxadiazol-3-yl]benzamide was obtained from reacting 1-butyl-1H-1,3-benzimidazole-2-carbonyl chloride and 2-chloro-1-benzene-carbonyl chloride, in 23 wt. % overall yield. $^1$H-NMR (DMSO-d$^6$) δ: 11.87 (1H, NH), 7.91-7.53 (8H, $C_{Aryl}$H), 4.73 (2H, d, N—$CH_2$), 1.89, 1.47 (2H, 2H, m, m, —$CH_2$—$CH_2$—), 0.99 (3H, d, $CH_3$).

Example 2

2-Chloro-$N^1$-[4-(1-isobutyl-1H-1,3-benzimidazol-2-yl)-1,2,5-oxadiazol-3-yl]benzamide was obtained from reacting 1-isobutyl-1H-1,3-benzimidazole-2-carbonyl chloride and 2-chloro-1-benzene-carbonyl chloride, in 27 wt. % overall yield. $^1$H-NMR (DMSO-d$^6$) δ: 11.92 (1H, NH), 7.96-7.53 (8H, $C_{Aryl}$H), 4.50 (2H, d, N—$CH_2$), 2.25 (1H, qnt, CH), 0.95 (6H, d, 2×$CH_3$).

Example 3

2-Chloro-$N^1$-[4-(1-allyl-1H-1,3-benzimidazol-2-yl)-1,2,5-oxadiazol-3-yl]benzamide was obtained from reacting 1-allyl-1H-1,3-benzimidazole-2-carbonyl chloride and 2-chloro-1-benzene-carbonyl chloride, in 12 wt. % overall yield. $^1$H-NMR (DMSO-d$^6$) δ: 11.81 (1H, NH), 7.94-7.33 (8H, $C_{Aryl}$H), 6.11 (1H, m, $H_2$C=CH), 5.38 (2H, d, N—$CH_2$), 5.19, 5.07 (1H, 1H, d, d, $H_2$C=CH).

Example 4

Ethyl 2-(2-4-[(2-fluorobenzoyl)amino]-1,2,5-oxadiazol-3-yl-1H-1,3-benzimidazol-1-yl)acetate was obtained from reacting ethyl 2-[2-(chlorocarbonyl)-1H-1,3-benzimidazol-1-yl]acetate and 2-fluoro-1-benzenecarbonyl chloride, in 19 wt. % overall yield. $^1$H-NMR (DMSO-d$^6$) δ: 12.15 (1H, NH), 8.15-7.39 (8H, $C_{Aryl}$H), 5.55 (2H, s, N—$CH_2$), 4.22 (2H, qrt, O—$CH_2$—), 1.28 (3H, t, $CH_3$).

Example 5

2-Ethoxy-$N^1$-[4-(4-methoxyphenyl)-1,2,5-oxadiazol-3-yl]benzamide was obtained from reacting 4-methoxy-1-benzenecarbonyl chloride and 2-ethoxy-1-benzenecarbonyl chloride, in 11 wt. % overall yield. $^1$H-NMR (DMSO-d$^6$) δ: 10.40 (1H, NH), 7.78-7.01 (8H, $C_{Aryl}$H), 4.20 (2H, qrt, O—$CH_2$—$CH_3$), 3.91 (3H, s, O—$CH_3$), 1.29 (3H, t, O—$CH_2$—$CH_3$).

Example 6

2-Propoxy-N$^1$-[4-(4-methoxyphenyl)-1,2,5-oxadiazol-3-yl]benzamide was obtained from reacting 4-methoxy-1-benzenecarbonyl chloride and 2-propoxy-1-benzene-carbonyl chloride, in 13 wt. % overall yield. $^1$H-NMR (DMSO-d$^6$) δ: 10.50 (1H, NH), 7.80-7.07 (8H, C$_{Aryl}$H), 4.10 (2H, t, O—CH$_2$—CH$_2$), 3.82 (3H, s, O—CH$_3$), 1.66 (2H, sext, O—CH$_2$—CH$_2$—CH$_3$), 0.92 (3H, d, O—CH$_2$—CH$_2$—CH$_3$).

Example 7

2-Ethoxy-N$^1$-[4-(4-ethoxyphenyl)-1,2,5-oxadiazol-3-yl]benzamide was obtained from reacting 4-ethoxy-1-benzenecarbonyl chloride and 2-ethoxy-1-benzenecarbonyl chloride, in 20 wt. % overall yield. $^1$H-NMR (DMSO-d$^6$) δ: 10.47 (1H, NH), 7.77-7.03 (8H, C$_{Aryl}$H), 4.23, 4.10 (2H, 2H, qrt, qrt, O—CH$_2$—CH$_3$, O—CH$_2$—CH$_3$), 1.37, 1.29 (3H, 3H, t, t, O—CH$_2$—CH$_3$, O—CH$_2$—CH$_3$).

Example 8

2-Propoxy-N$^1$-[4-(4-ethoxyphenyl)-1,2,5-oxadiazol-3-yl]benzamide was obtained from reacting 4-ethoxy-1-benzenecarbonyl chloride and 2-propoxy-1-benzene-carbonyl chloride in 9 wt. % overall yield. $^1$H-NMR (DMSO-d$^6$) δ: 10.48 (1H, NH), 7.75-7.01 (8H, C$_{Aryl}$H), 4.10 (4H, m, O—CH$_2$, O—CH$_2$), 1.69 (2H, sext, O—CH$_2$—CH$_2$—CH$_3$), 1.38 (3H, t, O—CH$_2$—CH$_3$), 0.92 (3H, d, O—CH$_2$—CH$_2$—CH$_3$).

Example 9

2-Butoxy-N$^1$-[4-(4-ethoxyphenyl)-1,2,5-oxadiazol-3-yl]benzamide was obtained from reacting 4-ethoxy-1-benzenecarbonyl chloride and 2-butoxy-1-benzene-carbonyl chloride, in 14 wt % overall yield. $^1$H-NMR (DMSO-d$^6$) δ: 10.48 (1H, NH), 7.76-7.02 (8H, C$_{Aryl}$H), 4.08 (4H, m, O—CH$_2$, O—CH$_2$), 1.69 (2H, sext, O—CH$_2$—CH$_2$—CH$_2$—CH$_3$), 1.38 (3H, t, O—CH$_2$—CH$_3$), 1.22 (3H, d, —CH$_2$—CH$_3$), 0.99 (3H, d, CH$_3$).

Example 10

2-Ethoxy-N$^1$-[4-(4-ethoxy-3-methylphenyl)-1,2,5-oxadiazol-3-yl]benzamide was obtained from reacting 4-ethoxy-3-methyl-1-benzenecarbonyl chloride and 2-ethoxy-1-benzenecarbonyl chloride, in 18 wt. % overall yield. $^1$H-NMR (DMSO-d$^6$) δ: 10.44 (1H, NH), 7.81-6.98 (8H, C$_{Aryl}$H), 4.23, 4.10 (2H, 2H, qrt, qrt, O—CH$_2$—CH$_3$, O—CH$_2$—CH$_3$), 2.20 (3H, s, CH$_3$), 1.40, 1.28 (3H, 3H, t, t, O—CH$_2$—CH$_3$, O—CH$_2$—CH$_3$).

Example 11

2-Propoxy-N$^1$-[4-(4-ethoxy-3-methylphenyl)-1,2,5-oxadiazol-3-yl]benzamide was obtained from reacting 4-ethoxy-3-methyl-1-benzenecarbonyl chloride and 2-propoxy-1-benzene-carbonyl chloride, in 20 wt. % overall yield. $^1$H-NMR (DMSO-d$^6$) δ: 10.47 (1H, NH), 7.82-6.99 (8H, C$_{Aryl}$H), 4.08 (4H, m, O—CH$_2$, O—CH$_2$), 2.19 (3H, s, CH$_3$), 1.63 (2H, sext, O—CH$_2$—CH$_2$—CH$_3$), 1.40 (3H, t, O—CH$_2$—CH$_3$), 0.90 (3H, d, O—CH$_2$—CH$_2$—CH$_3$).

Example 12

5-chloro-N$^2$-[4-(4-ethoxyphenyl)-1,2,5-oxadiazol-3-yl]-3-methyl-1-benzofuran-2-carboxamide was obtained from reacting 4-ethoxy-1-benzenecarbonyl chloride and 5-chloro-3-methyl-1-benzofuran-2-carbonyl chloride, in 12 wt. % overall yield. $^1$H-NMR (DMSO-d$^6$) δ: 10.48 (1H, NH), 7.75-7.01 (8H, C$_{Aryl}$H), 4.10 (4H, m, O—CH$_2$, O—CH$_2$), 1.69 (2H, sext, O—CH$_2$—CH$_2$—CH$_3$), 1.38 (3H, t, O—CH$_2$—CH$_3$), 0.92 (3H, d, O—CH$_2$—CH$_2$—CH$_3$).

Among 546 compounds advanced into follow-up screen 22 compounds showed activity <10 uM and 12 compounds of the above mentioned examples—<1 uM (Table 1). IC$_{50}$ represents the concentration of a drug that is required for 50% inhibition in vitro. As shown in Table 1, the compositions at the beginning of the table are more effective inhibitors than those at the end of the table.

TABLE 1

| Example # | IC$_{50}$, μM |
|---|---|
| 1 | 0.29 |
| 2 | 0.28 |
| 3 | 0.89 |
| 4 | 0.32 |
| 5 | 0.98 |
| 6 | 0.85 |
| 7 | 0.12 |
| 8 | 0.34 |
| 9 | 0.85 |
| 10 | 0.86 |
| 11 | 0.93 |
| 12 | 0.95 |

Protocol for Cell Proliferation Assay:

This homogeneous assay involves simply adding a single reagent, the Alamar-Blue to the cell culture and measuring the fluorescence intensity (excitation wavelength=530 nm, emission wavelength=590 nm) after an incubation step. The Alamar-Blue reagent utilizes the redox dye resazurin, which is not fluorescent, but upon reduction by metabolically active cells is converted into a highly fluorescent product (resorufin). A decrease in fluorescence in the presence of a test compound indicates reduced proliferation. This change in signal is proportional to the number of viable cells and used as a measure of relative cytotoxicity. Therefore, the fluorescence intensity observed in this assay is a true measure of the viable proliferative cells.

Reagents
  2 mM stock of Paclitaxel in DMSO.
  DMSO—(dimethylsulfoxide) (Panreac, Cat. number 141954.1611)
  Resazurin sodium salt (Sigma, R-7071). 50 mM stock in DMSO.
Equipment
  Biomek FX Laboratory Automated Workstation (Beckman Coulter Inc., Fullerton, Calif.)
  CO$_2$ incubator (VWR Science, USA)
  Bright line Hemacytometer (Z359629, Sigma, Ill., USA)
Materials
  384-deep well plates (Greiner, No 781270)
  384-well optical bottom tissue culture plates (Greiner, No. 82051-282)
Propagation
CONDITIONS: 37° C., air 95%; carbon dioxide (CO$_2$) 5%, humidified atmosphere.
SUBCULTURING:
  Cells were grown in 175 cm$^2$ flasks to 90-100% of confluency.
  Culture media (RPMI-1640 (Paneco, C310)+10% FBS (fetal bovine serum)) was aspirated and cell layer was briefly rinsed with 0.53 mM EDTA solution to remove all traces of serum.

2 ml of 0.2% trypsin/0.53 mM EDTA (ethylenediamine-tetraacetic acid) solution was added to cells.

Flasks were returned to incubator for 5 rain to allow cells detachment

Add 6.0 ml of complete growth medium.

Single cell suspension was created by gently pipetting.

Cells are counted using a Hematocytometer and suspension with desirable cell concentration is prepared.

To test proliferation inhibition DU-145 cells were plated in 384-well plate at the density 4000 cells/well. Next day 4 mM solutions of compounds in DMSO were diluted 100 times in medium and added to cells to final concentration 20 uM (40 ul of cells+40 ul of compounds). Taxol at final concentration 1 uM was used as positive control. Cells were incubated with compounds for 3 days. After that Alamar-Blue was added to cells to a final concentration of 50 uM. After incubation for 4-6 hours at 37° C., fluorescence in plate was read using fluorescence plate reader Wallac 1420 (530 nm excitation filter, 590 nm emission filter). Proliferation inhibition was calculated using formula:

$$\% INH = 100 * ((F_{negative} - \text{compound signal})/(F_{negative} - F_{positive})),$$

$F_{negative}$—DMSO was added to cells (viable cells)

$F_{positive}$—taxol (1 uM) was added to cells (number of cells at the first day of incubation)

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A compound having the structural Formula (I),

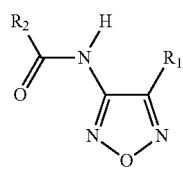
(I)

tautomers or pharmaceutically acceptable salts thereof, wherein:

R1 is a substituted heteroaryl fused to a substituted or non-substituted aromatic ring to form a bicyclic heterocycle of the formula (III):

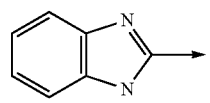
(III)

having a substitution on at least one of the nitrogen atoms, wherein at least one of the nitrogen atoms is substituted with a $C_3$-$C_4$ straight-chain or branched alkane or alkene; and, R2 is selected from substituted or non-substituted aryls, fused or non-fused to substituted or non-substituted aromatic ring, aryl or heteroaryl groups.

2. The compound of claim 1, wherein the compound is selected from the group consisting of:

2-Chloro-$N^1$-[4-(1-butyl-1H-1,3-benzimidazol-2-yl)-1,2,5-oxadiazol-3-yl]benzamide;

2-Chloro-$N^1$-[4-(1-isobutyl-1H-1,3-benzimidazol-2-yl)-1,2,5-oxadiazol-3-yl]benzamide; and 2-Chloro-$N^1$-[4-(1-allyl-1H-1,3-benzimidazol-2-yl)-1,2,5-oxadiazol-3-yl]benzamide.

3. The compound of claim 1, wherein R2 is a substituted aryl group.

4. A pharmaceutical composition comprising a compound having the structural Formula (I),

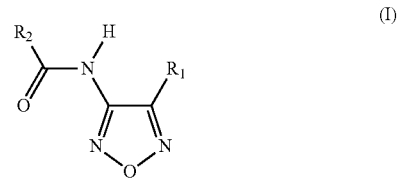
(I)

tautomers, or pharmaceutically acceptable salts thereof, wherein:

R1 is a substituted heteroaryl fused to a substituted or non-substituted aromatic ring to form a bicyclic heterocycle of the general formula (III):

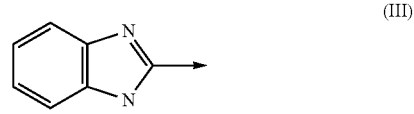
(III)

having a substitution on at least one of the nitrogen atoms, wherein at least one of the nitrogen atoms is substituted with a $C_3$-$C_4$ straight-chain or branched alkane or alkene; and, R2 is selected from substituted or non-substituted aryls, fused or non-fused to substituted or non-substituted aromatic ring, aryl or heteroaryl groups, and a pharmaceutical carrier.

5. The compound of claim 4, wherein the compound is selected from the group consisting of:

2-Chloro-$N^1$-[4-(1-butyl-1H-1,3-benzimidazol-2-yl)-1,2,5-oxadiazol-3-yl]benzamide;

2-Chloro-$N^1$-[4-(1-isobutyl-1H-1,3-benzimidazol-2-yl)-1,2,5-oxadiazol-3-yl]benzamide; and 2-Chloro-$N^1$-[4-(1-allyl-1H-1,3-benzimidazol-2-yl)-1,2,5-oxadiazol-3-yl]benzamide.

6. The compound of claim 4, wherein R2 is a substituted aryl group.

* * * * *